(12) United States Patent
Busam et al.

(10) Patent No.: US 6,642,430 B1
(45) Date of Patent: Nov. 4, 2003

(54) METHOD FOR APPLYING A FOAMABLE MOVEMENT OBSTRUCTION AGENT TO AN ABSORBENT MEMBER

(75) Inventors: Ludwig Busam, Hünstetten (DE); Michael Divo, Friedrichsdorf (DE); Torsten Lindner, Kronberg (DE); Thomas Tombult-Meyer, Nettersheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/936,400
(22) PCT Filed: Apr. 26, 2000
(86) PCT No.: PCT/US00/11288
§ 371 (c)(1),
(2), (4) Date: Sep. 11, 2001
(87) PCT Pub. No.: WO00/64396
PCT Pub. Date: Nov. 2, 2000

(30) Foreign Application Priority Data

Apr. 28, 1999 (EP) .............................................. 99108317

(51) Int. Cl.⁷ ................................................. A61F 13/15
(52) U.S. Cl. ..................................... 604/368; 604/369
(58) Field of Search ................................... 604/381, 382, 604/385.01, 369, 368

(56) References Cited

U.S. PATENT DOCUMENTS

| | | | |
|---|---|---|---|
| 4,610,678 A | | 9/1986 | Goldman et al. |
| 5,342,858 A | | 8/1994 | Litchholt et al. |
| 5,652,194 A | * | 7/1997 | Dyer et al. |
| 5,763,067 A | * | 6/1998 | Bruggemann et al. |
| 5,843,059 A | * | 12/1998 | Niemeyer et al. |
| 5,873,867 A | * | 2/1999 | Coles et al. |
| 6,033,769 A | * | 3/2000 | Brueggemann et al. |
| 6,060,637 A | * | 5/2000 | Bitowft et al. |
| 6,426,445 B1 | * | 7/2002 | Young et al. |

FOREIGN PATENT DOCUMENTS

| | | |
|---|---|---|
| EP | 0 846 455 A1 | 6/1998 |
| EP | 0 875 225 A1 | 11/1998 |
| WO | WO 98/43580 | 10/1998 |

\* cited by examiner

*Primary Examiner*—Dennis Ruhl
(74) *Attorney, Agent, or Firm*—Douglas W. McArthur; Ian S. Robinson; Ken K. Patel

(57) ABSTRACT

The invention is a method applying a foamable movement obstruction agent to an absorbent article which comprises superabsorbent material. The foamable agent can be applied before, after, or simultaneously to creation of the foam structure, and can be applied to the article directly or to a carrier substrate to then be combined with the article.

27 Claims, 3 Drawing Sheets

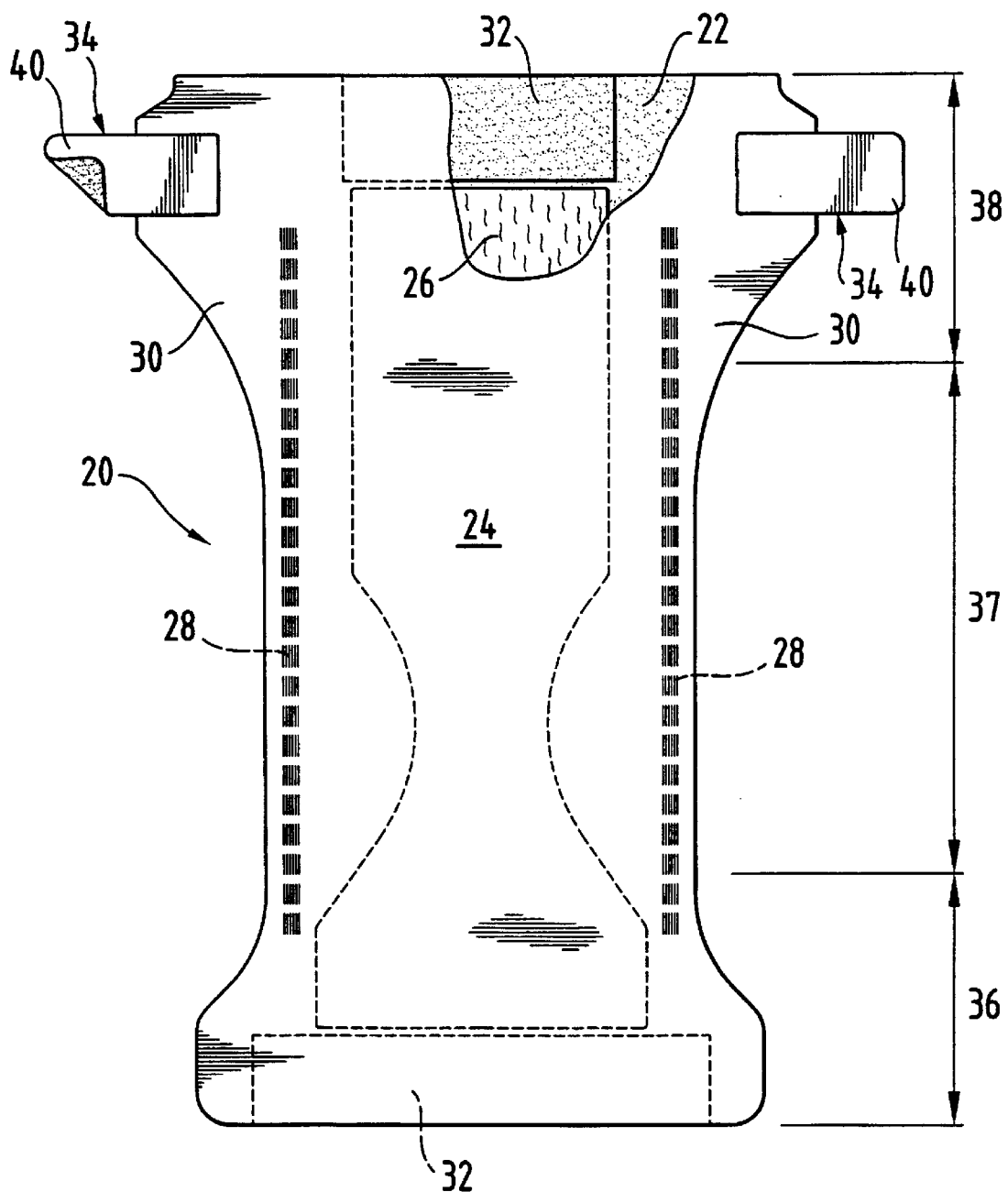

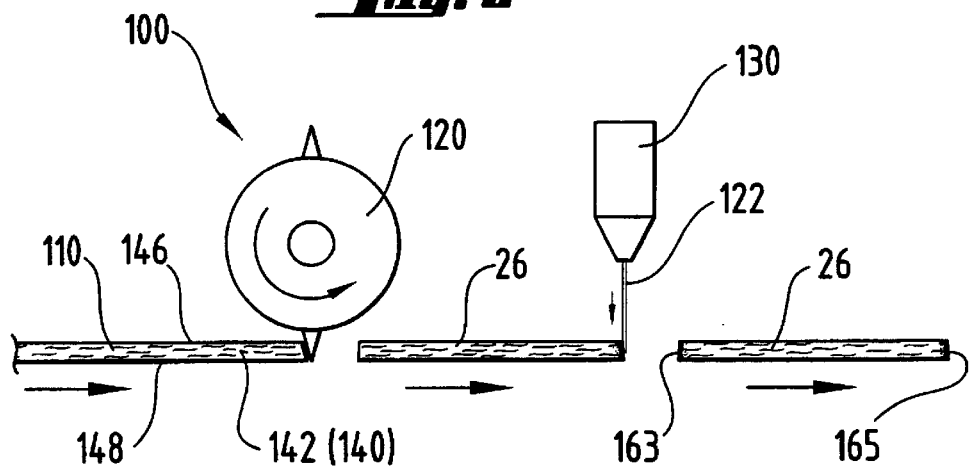
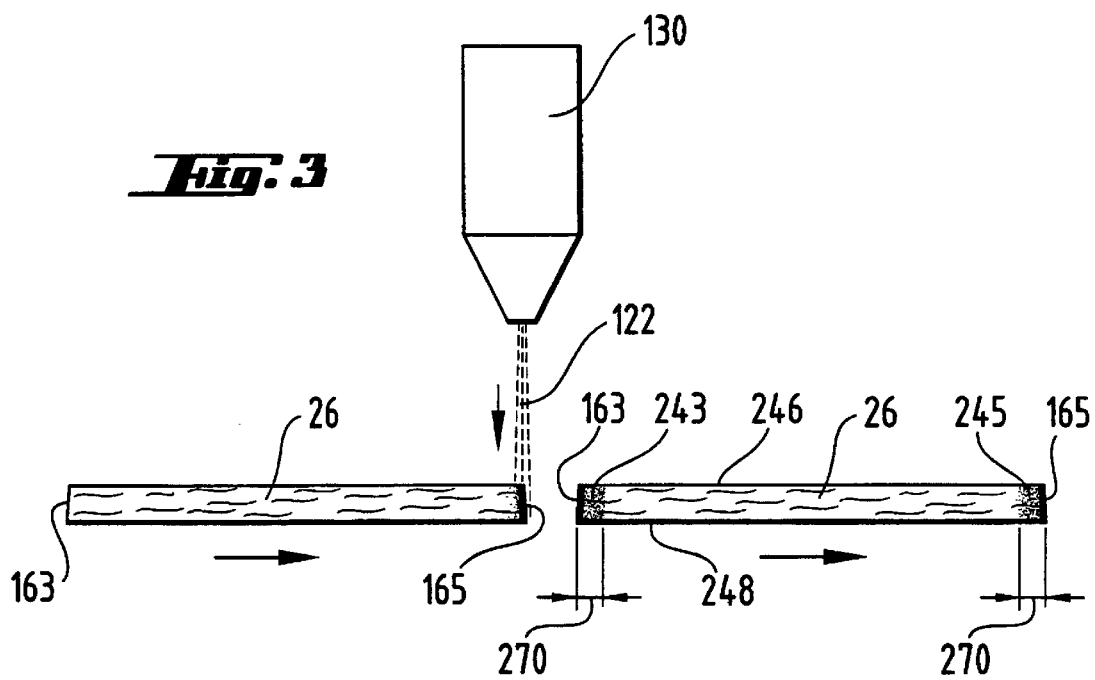

METHOD FOR APPLYING A FOAMABLE MOVEMENT OBSTRUCTION AGENT TO AN ABSORBENT MEMBER

FIELD OF THE INVENTION

This invention relates to a method for integrity and immobilization enhancement for an absorbent member, and more particularly to a method for applying a foamable movement obstruction agent to an absorbent member which is suitable for use in an absorbent core for a disposable absorbent article.

BACKGROUND OF THE INVENTION

Absorbent cores which comprise porous members, such as fibrous batts or foamed structures, are well known in the art. Such cores can imbibe liquids, such as discharged body fluids, both by an absorption mechanism wherein fluid is taken up by the porous material itself and by a wicking mechanism wherein fluid is acquired by, distributed through and stored in the capillary interstices. One means for improving the absorbency characteristics of such porous structures is to incorporate therein superabsorbent material, such as polymeric gelling material (also referred to as hydrogel-forming material superabsorbent polymers, etc.) which imbibe fluid. The superabsorbent material serves to retain fluid such as discharge body liquids. An absorbent structure of this type wherein hydrogel-forming materials in particulate form are incorporated into fibrous webs is disclosed in Weisman and Goldman, U.S. Pat. No. 4,610,678, issued Sep. 9, 1986. The combination of superabsorbent materials with foamed structures is, for example, described in U.S. patent application Ser. No. 09/041,930, filed Mar. 13, 1998.

The improvement in absorbency provided by incorporation of absorbent gelling materials has permitted the realization of absorbent articles, such as disposable diapers, which employ relatively thin absorbent cores and which are, therefore, relatively thin products.

Notwithstanding the existence of absorbent cores as described above, there remains a need to provide absorbent cores which reduce and preferably eliminate the phenomena referred to as gel-on-skin. Gel-on-skin is the situation where absorbent gelling materials escape from the absorbent core and travel through the bodyside liner or topsheet of the absorbent article where they come into contact the wearer's skin.

In one class of prior art continuous lay down operations, fibers and superabsorbent materials are mixed together in a continuous web. The continuous web is then cut into individual absorbent members or cores. The individual absorbent members are then placed between a liquid pervious topsheet and a liquid impervious backsheet to form an absorbent article. However, this configuration provided an unsatisfactory product as absorbent gelling material easily penetrated through the topsheet creating unacceptable amounts of gel-on-skin.

One solution to the above continuous lay down operation, was to place another web, such as a tissue or nonwoven web on top of the continuous web and then cut both the tissue and continuous web into individual members comprising the core and the tissue. The individual members were then placed in the product with the tissue positioned between the topsheet and the absorbent core substantially preventing absorbent gelling material from escaping from the uppermost surface of the absorbent core and thus reducing the amount of gel-on-skin.

However, when for example, the tissue and the continuous web are cut into individual members, the ends of the absorbent core are left open, i.e., the ends of the absorbent core are not covered by the tissue, allowing absorbent gelling material to escape through the ends of the absorbent core.

Similarly, gel-on-skin can occur, if the absorbent articles are formed discretely, i.e. if individual cores are formed for example on a lay-down screen or a lay-down drum, such a described in EP-A-0.478.182. Such cores can be transferred to carrier like tissues or non-wovens to further be integrated into absorbent articles, and such cores also can exhibit before, during or after enveloping as well as during use an undesirable degree of superabsorbent particles being released from the end zones thereof.

Further, gel-on-skin can occur, when foamed materials are combined with superabsorbent materials, such as in U.S. patent Ser. No. 09/041 930, filed Mar. 13, 1998. In such designs, the foam material can be in particulate form, and can be mixed with the superabsorbent material, or the foamed material may be in a layered or sheet like form, and the superabsorbent can be attached thereto.

Hence, it is an object of this invention to provide method of improving the integrity and the immobilization of superabsorbent by reducing the mobility of various absorbent member elements of an absorbent article.

Preferably such a method should be versatile and allow readily adjustment to various changes of the design of the article, yet it should be easy to use.

It is a further object of the present invention to achieve such improvements without detrimental effect on the liquid handling capabilities of the article, and even more preferably to improve the liquid handling capability of the article.

BRIEF SUMMARY OF THE INVENTION

The invention is a method for making an absorbent member comprising superabsorbent material, including the step of applying a foamable movement obstruction agent. More particular, it is a method for making an absorbent article including (a) a first step of providing an absorbent member comprising a superabsorbent material and a foamable agent; and then the steps of (b) foaming said foamable agent, and (c) applying said foamable agent to said absorbent member. The sequence of the steps (b) and (c) can be any of either (b) before (c), or (c) before (b), or (b) and (c) simultaneously.

Upon application of this method, the foamable agent provides a movement obstruction means for the superabsorbent material. The superabsorbent material can be particulate, and the absorbent member can further comprise fibrous material, or can comprise open cell polymeric foam material, preferably of the High Internal Phase Emulsion (HIPE) type.

The foamable agent can have a tack or adhesion behavior at least to the superabsorbent and at least during or after the application phase, such as by being an adhesive. The foamable agent can comprise material selected from the group of natural or synthetic polymeric solutions or emulsions. The foamable agent can be a thermoplastic polymer or polymeric composition having a softening point in the range between 50° Celsius and 300° Celsius, and can be a wax or a composition containing at least 50% by weight of a wax. In an alternative embodiment, the foamable agent can be a thermo-set polymer or polymeric composition, such as by comprising polyurethane compositions, or polyurethane prepolymers, which are activated by the addition of initiating chemicals, preferably ambient moisture, or initiating energy, preferably heat or radiation. This activation can be achieved simultaneously to the foaming step.

The foamable agent can be applied to the absorbent member directly, or to a substrate, such as a tissue or a nonwoven wrap, which is combined with the absorbent member after the application of the foaming agent.

The foamable agent can be applied to the absorbent member so as to cover major portions of the surface of the member, such as more than 90% of the total surface of said absorbent member.

Alternatively, the foamable agent can be applied to selected regions of the absorbent member, such as to opposing ends in discrete, spaced apart sealing zones. For these designs, the foamable agent preferably covers less than about 25%, preferably less than 10% and even more preferably less than 5% of the total surface of the absorbent member. In such designs, the foamable agent can be applied in a strip along the edge of the absorbent member having a width of less than about 5 cm, preferably of less than 1 cm. The foamable agent can also penetrate into the structure of the absorbent member.

The foamable agent can remain in the foam structure after the article is manufactured, or the foamed structure can collapse or reticulate after it has been foamed and applied.

The absorbent member can be an individual absorbent member, which can further be wrapped with one or more wrapping materials, which can be bonded by the foamable agent to said absorbent member or to themselves

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIG. 1 is a plan view of an absorbent article comprising an individual absorbent core manufactured in accordance with the one embodiment of the method of the present invention.

FIG. 2 is a simplified schematic illustration of a continuous lay down method for sealing absorbent cores according to one embodiment of the present invention.

FIG. 3 is an simplified schematic enlarged cross-sectional illustration of the application of foam movement obstruction agent to the individual absorbent members.

DETAILED DESCRIPTION OF THE INVENTION

Figure 4:
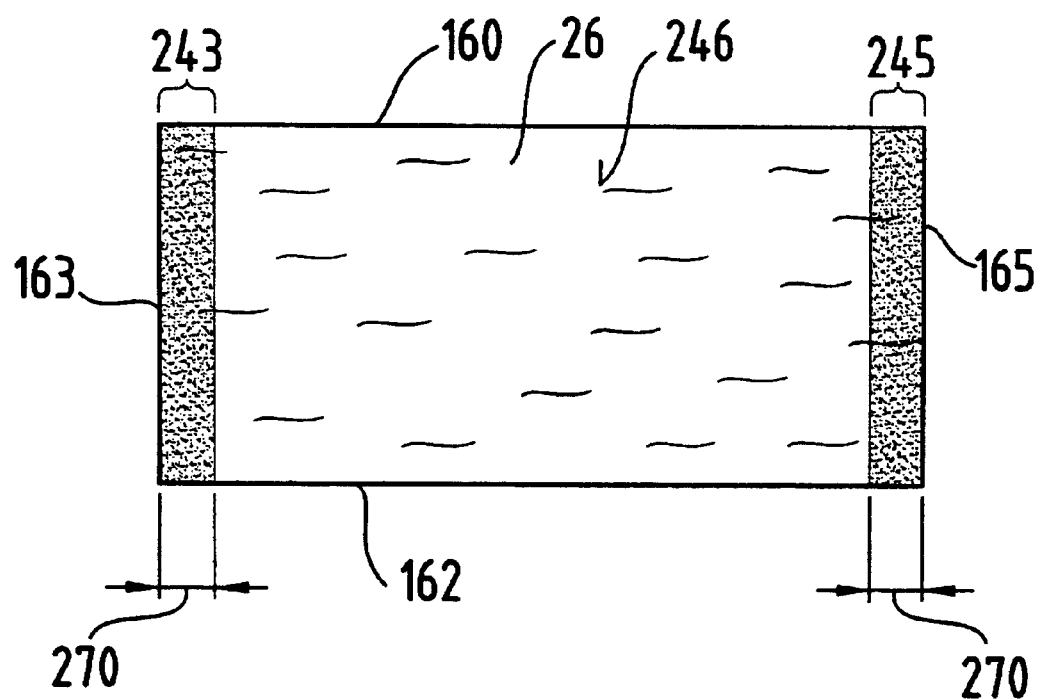
FIG. 4 is a plan view of an individual absorbent member after the application of superabsorbent material movement obstruction agent.

The method of the present invention is particularly suitable for manufacturing absorbent cores for use in disposable absorbent articles. As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

A preferred embodiment of a unitary absorbent article comprising an absorbent core manufactured by using the method of the present invention, is the unitary disposable absorbent article, diaper 20, shown in FIG. 1. As used herein, the term "diaper" refers to an absorbent article generally worn by infants and adult incontinent persons and is worn about the lower torso of the wearer. It should be understood, however, that the present invention is also applicable to other absorbent articles such as incontinence briefs, incontinence undergarments, absorbent inserts, diapers holders and liners, feminine hygiene garments, and the like. It also should be understood, that the various embodiments can be applied in parallel, i.e. unless explicitly stated, these are non-exclusive embodiments.

With reference to FIG. 1, an absorbent article, such as a diaper 20, generally comprises a liquid pervious topsheet 22, a liquid impervious backsheet 24 joined with the topsheet 22; and an absorbent core 26 intermediate the topsheet 22 and the backsheet 24. The diaper 20 preferably further comprises a front waist region 36, a rear waist region 38, a crotch region 37 positioned between the front waist region 36 and the rear waist region 38, elasticized leg cuffs 28, ear flaps 30, an elastic waist feature 32 and a fastening system 34 comprising at least one tape tab 40. An example of a suitable absorbent article to which the absorbent core of the present invention may be inserted is more fully and completely described in U.S. Pat. No. 5,151,092 issued to Buell et al. on Sep. 29, 1992.

The absorbent core 26 of the present invention may be produced on the apparatus 100, as shown in FIG. 2 as one exemplary embodiment. Therein, the apparatus 100 is integrated into a disposable absorbent article manufacturing line such that the absorbent core 26 of the present invention may be manufactured "on-line". (As used herein, the term "integrated" means interconnected process modules that operate concurrently to produce finished products from source materials. The term "on-line" is used to refer to the process of manufacturing the absorbent cores of the present invention on an apparatus that is integrated with the manufacturing line that produces the disposable absorbent articles to which the tape tabs will be joined.)

Examining apparatus 100 in greater detail, a web 110 is provided. Web 110 comprises fibrous material and superabsorbent material. The fibrous material may comprise cellulose fibers, in the form of fluff; modified cellulose fibers such as stiffened cellulose fibers; synthetic fibers such as those made of cellulose acetate, polyvinyl fluoride, polyvinylidene chloride, acrylics, polyvinyl acetate, non-soluble polyvinyl alcohol, polyethylene, polypropylene, polyamides (such as nylon), polyesters, bi-component fibers, tri-component fibers, mixtures thereof and the like. Preferred synthetic fibers have a denier of from about 3 denier per filament to about 25 denier per filament, more preferably from about 5 denier per filament to about 15 denier per filament. Also preferably, the fiber surfaces are hydrophilic or are treated to be hydrophilic.

Suitable superabsorbent materials include but are not limited to discrete particles of absorbent gelling material and superabsorbent fibrous material such as acrylate grafted fibers and superabsorbent modified fibers. The superabsorbent material can be in any form which can be incorporated into a flexible web or sheet to form the web 110. The superabsorbent material, upon contact with fluids such as water or body fluids, absorb such fluids. The superabsorbent material is typically in the form of discrete particles of absorbent gelling material.

Continuous web 110 is fed to knife 120 in the direction indicated by the arrows shown in FIG. 2. Web 110 has a first or uppermost surface 146, an opposing second or lowermost surface 148, a first side edge 140 (not shown in FIG. 2), and an opposing second side edge 142. Knife 120 cuts the web into individual absorbent members 26 having a pair of opposing cut ends. The individual absorbent members 26 are then fed to applicator 130 which applies a superabsorbent material movement obstruction agent 122 to the individual absorbent members 26.

Of course other webs may be fed with continuous web 110 to knife 120. For example, a tissue or nonwoven web may be positioned adjacent the first surface 146 and/or the second surface 148 and the composite is then fed to knife 120. However, for simplicity, only a single web 110 is shown in FIG. 2.

As an alternative to the cutting operation with knife 120, any process can be used that provides individual absorbent members to the applicator 130. For example, a discrete absorbent member formation process can be used, such as described in EP-A-0.478.182, or U.S. Pat. No. 4,952,708, the disclosure of both publications being incorporated herein by reference.

The absorbent member may also comprise in addition to the foam movement obstruction agent (as described hereinafter) an absorbent element in a foamed form, generally in prefabricated form. Particularly preferred foam absorbent materials are open cell foam, and even more preferably of the HIPE (High internal phase emulsion) type, such as described in U.S. patent application Ser. No. 09/041,930, filed Mar. 13, 1998. Such foams may be in the particulate shape, or may be in an essentially two-dimensionally extending sheet or layer form. The particulate foams can be mixed with superabsorbent materials, whereas in the case of sheeted foam materials, the superabsorbent materials can be attached to the foam by conventional means such as conventional gluing, or moisture bonding, or mechanical entrapment, and the foam movement obstruction means can be an additional means for improving immobilization.

The articles according to the present invention comprise a "foamable movement obstruction agent". This term refers to a material which is applied to the article so as to reduce the potential for relative movement, in particular for relative movement of absorbent elements of the absorbent member of the absorbent article. This agent is applied during the manufacturing of the absorbent member or article, and has at least for one step in this process, in a foam structure. A foam structure refers to a two phase structure, wherein a plurality of gas filled voids are circumscribed by lamella of the agent.

Referring now to FIGS. 3 and 4, relating to one particular embodiment of the present invention, the absorbent members 26 have first and second end edges 163 and 165 corresponding to the cut ends of the web 110, a first side edge 160, a second side edge 162, a first or uppermost surface 246, and a second or lowermost surface 248.

In this embodiment, foamable movement obstruction agent 122 is applied only to the ends of the individual absorbent members 26. The foamable movement obstruction agent 122 can be applied directly to the end edges 163 and 165, in a foamed formed or in liquid form to be foamed after application. The foamable movement obstruction agent 122 may be applied to the first or uppermost surface 246 directly over the end edges 163 and 165 and then allowed to migrate through the member 26 from the first surface 246 to the second surface 248. Alternatively, the foamable movement obstruction agent 122 may be applied to both the end edges 163 and 165 and the uppermost surface 246. Yet another alternative for application of the foamable movement obstruction agent is the application of the foam to a substrate such as a carrier or enveloping tissue or non-woven web, or a topsheet or a backsheet, if these are in direct contact with the absorbent core. Then, prior to the contacting step, the foamable agent can be applied to the carrier, and can either penetrate into the member and thus may even form an interpenetrating network in addition to a fibrous network, if existent, or reside on the surface without penetrating into the member (at least not to a large extent). There it may form a reticulated network with reticulated struts of materials circumscribing the pores, or it can form a foamed structure with two-dimensional pore walls. These walls can form closed cell type foams or open cell foams, which, in combination with wetting and wicking properties of the foamable agent for the use liquid, may be selected according to the intended use. For example, where in addition to the movement obstruction properties also liquid flow blockage means for example for urine is desired, a closed cell foam may be used, or a hydrophobic open cell foam. If the layer is desired to provide enhance liquid distribution and/or wicking properties, a hydrophilized open cell foam may be desired, for example of the described HIPE type.

In yet another embodiment, the foamable movement obstruction agent can remain in the foam structure and absorbent materials such as in the form of superabsorbent, and in particular particulate superabsorbent, may penetrate into the foam cells. In an alternative to this embodiment, the foam wall may reticulate thus then forming struts to form an movement obstruction agent matrix with absorbent material therein.

The foamable movement obstruction agent can be prepared by any conventional means for creating and applying a foam to or on a substrate. Thus, the foam can be created by mechanical agitation just prior to application. Alternatively, the foamed agent can foam up just upon application of an essentially unfoamed material, for example by comprising a blowing agent, which is kept for example in a dissolved form under an increased pressure until the application, and which is being released upon removal of the increased pressure during the application step. In an even further alternative, the blowing agent can be maintained in the unfoamed agent even after application, and is released in a separate step, such as an increase in temperature, or is created after application such as by reaction with ambient moisture. Various publications disclose suitable application processes, such as U.S. Pat. No. 4,423,161, or U.S. Pat. No. 5,342,858.

The foamable movement obstruction agent can be applied in and remain in a foamed structure, which can be squeezed towards the end portions of the core, thereby providing a complete foam sealing cap of foam, or it can penetrate into the absorbent material by capillary wicking action, or it can form a reticulated two- or three-dimensional material network, in particular if the foamed agent is of an adhesive type. The foamable agent can also remain in a open or closed cell foamed structure, and at least parts of the absorbent material may be embedded within the foam cells. Similarly, the reticulated network may entangle absorbent material.

In the embodiment of application of the foamable movement obstruction agent 122 to only the end edges 163 and 165, each individual absorbent member 26 can have a pair of discrete, spaced apart sealing zones 243 and 245. Zone 243 is located adjacent first end edge 163 and zone 245 is located adjacent end edge 165. For typical absorbent article of the baby diaper type, the zones 243 and 245 of foaming means application can have a width dimension 270 of less that about 10 cm, typically less than about 5 cm, or even less than about 1 cm. Whilst the foamable movement obstruction agent can be applied to the entire web or absorbent member, a preferred embodiment is to apply it only in discrete, spaced apart zones. While the foamable movement obstruction agent does provide the benefit of obstructing the movement of the superabsorbent material through the cut end of a web, it may have some negative effects if applied to the entire web. For example, the agent may increase the stiffness of the web such that it becomes uncomfortable for the wearer if applied to the entire web. The agent may inhibit some of the absorbent properties of the web and thus would negatively impact the absorbent article which employed a web having the agent applied to the entire web. Thus, in order to achieve the desired effect of obstructing the movement of the superabsorbent material through the cut end of a web without negatively impacting the performance, comfort or other properties and characteristics of the web and an absorbent article which employs such a web, the superabsorbent material movement obstruction agent is preferably applied to the web in only discrete, spaced apart zones. When incorporated into an absorbent article, such as diaper 20 shown in FIG. 1, zones 243 and 244 of absorbent member 26 it can be advantageous to position the application of the foam movement obstruction agent only in the front waist region 36 and the rear waist region 38, respectively. Alternatively, the foamable movement obstruction means may cover more of the surfaces of the absorbent member, possibly all of the surfaces, provided the liquid handling properties such as urine acquisition and the like are not detrimentally affected.

As can be seen in FIG. 3 showing one particular embodiment of the present invention, wherein the foamable movement obstruction agent extends along the end edges 163 and 165 through the entire absorbent member 26 from the first surface 246 to the second surface 248. In one embodiment, zones 243 and 245 can occupy less than 30% of the volume of absorbent member 26, typically less than 20% of the volume of absorbent member 26, or even less than 10% of the volume of absorbent member 26. The foamable movement obstruction agent may penetrate through all of the absorbent member, or various part thereof.

Suitable foamable movement obstruction agents include, but are not limited, to polymeric solutions or emulsions, both natural (e.g. natural rubber latex) and synthetic, in which the liquid is water or any other suitable liquid or mixture of liquids. Waterborne emulsions are preferred and more preferred are waterborne emulsions of acrylic or vinylic adhesive polymers.

Other suitable agents for the foam movement obstruction agent also include thermoplastic polymers or polymeric compositions having a softening point, as determined by the ASTM Method D-36 "Ring and Ball", in the range between 50° C. and 300° C. Such thermoplastic polymer or polymeric composition can be a wax or a composition containing at least 50% by weight of a wax, such wax or composition preferably having a softening point less than about 180° C. More preferably such thermoplastic agent (being it a polymer, a wax or a composition derived therefrom) is or contains at least 50% by weight of a copolymer having, at least as one of its comonomers, acrylic acid, acrylamide, acrylic esters and/or derivatives therefrom.

Other suitable agents for the foamable obstruction agent can be thermo-set materials, especially of the polyurethane type. Such polymers can comprise aromatic end groups, but are preferably of the type with aliphatic endgroups. Such polymers can be applied in a pre-polymerized state, which can react upon application of a chemical initiator (such as ambient moisture) or by application of energy, such as in the form of heat, or radiation, and the like. Such polymers can create the foam structure during this reaction or they can be formed into a foam structure and then the reaction can be initiated.

The absorbent articles comprising such foamable movement obstruction agents show reduced tendency for gel-on-skin occurrence, such as can be demonstrated by shaking such articles manually or by a suitable shaking apparatus, and monitoring the amount of superabsorbent material, such as by using a sufficiently sized catch-pan or plate.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an absorbent article, said method comprises the steps of:
   (a) first providing an absorbent member having opposing ends comprising a superabsorbent material,
   (b) foaming a foamable agent,
   (c) and applying said foamable agent to said absorbent member, either in any sequence of (b) before (c), or (c) before (b), or (b) and (c) simultaneously; wherein said foamable agent is applied to said opposing ends in discrete, spaced apart sealing zones; whereby said foamable agent provides a movement obstruction means for the superabsorbent material.

2. A method according to claim 1, wherein said superabsorbent material is in particulate form.

3. A method according to claim 1, wherein said absorbent member further comprises fibrous material or absorbent open cell polymeric foam material.

4. A method according to claim 3, wherein said open cell polymeric foam material, is of the High Internal Phase Emulsion (HIPE) type.

5. A method according to claim 1, wherein said foamable agent has tack or adhesion at least to the superabsorbent material at least during or after the application step.

6. A method according to claim 5, wherein said foamable agent is an adhesive.

7. A method according to claim 1, wherein foamable agent is a material selected from the group of natural or synthetic polymeric solutions or emulsions, or mixtures thereof.

8. A method according to claim 1, wherein said foamable agent is a thermoplastic polymer or polymeric composition having a softening point in the range between 50° Celsius and 300° Celsius.

9. A method according to claim 8, wherein said thermoplastic polymer or polymeric composition is a wax or a composition containing at least 50% by weight of a wax.

10. A method according to claim 7, wherein said foamable agent is a thermo-set polymer or polymeric composition.

11. A method according to claim 10, wherein said foamable agent comprises polyurethane polymer.

12. A method according to claim 11, wherein said foamable agent comprises poly-urethane pre-polymers, and said method comprises further the step of activating said pre-polymers, wherein the step of activating comprises one or more acts selected from the group comprising addition of initiating chemicals, addition of ambient moisture, and addition of energy.

13. A method according to claim 12, wherein said step of activating said pre-polymers is simultaneous to foaming step.

14. A method according to claim 1, wherein said foamable agent is applied to the absorbent member directly.

15. A method according to claim 1, further comprising the steps of providing a substrate and combining said substrate with said absorbent member (26), wherein said foamable agent (122) is applied to said substrate prior to the combination with the absorbent member.

16. A method according to claim 1, wherein said sealing zones have a width of less than about 5 cm, preferably of less than 1 cm.

17. A method according to claim 1, wherein said foamable agent is applied to less than 10% of the total surface of said absorbent member.

18. A method according to claim 15, wherein said foamable agent is covering more than 90% of the total surface area of said absorbent member.

19. A method according to claim 1, further comprising the step of collapse or reticulation of the foamable agent after it has been foamed and applied to said absorbent member.

20. A method according to claim 1, wherein said foamable agent penetrates into the absorbent member.

21. A method according to claim 1, wherein said absorbent member is an individual absorbent member.

22. A method according to claim 21, wherein said individual absorbent member further comprises a wrapping substrate bonded by said foamable agent to said absorbent member or to itself.

23. A method according to claim 12, wherein the act of adding energy comprises one or more acts selected from adding heat and adding radiation.

24. A disposable absorbent article prepared according to the method of claim 1.

25. A disposable absorbent article according to claim 24, wherein said foamable movement obstruction agent is foamed adhesive.

26. A disposable absorbent article according to claim 25, wherein said foamable agent comprises polyurethane polymers.

27. A disposable absorbent article according to claim 24, wherein the article is a diaper.

* * * * *

UNITED STATES PATENT AND TRADEMARK OFFICE
CERTIFICATE OF CORRECTION

PATENT NO.    : 6,642,430 B1
DATED         : November 4, 2003
INVENTOR(S)   : Ludwig Busam et al.

It is certified that error appears in the above-identified patent and that said Letters Patent is hereby corrected as shown below:

Column 7,
Line 7, delete "that about 10 cm," and insert -- than about 10 cm, --.
Line 66, delete "comonomers," and insert -- co-monomers, --.

Signed and Sealed this

Fourteenth Day of February, 2006

JON W. DUDAS
*Director of the United States Patent and Trademark Office*